United States Patent [19]
Ganhy

[11] Patent Number: 5,475,177
[45] Date of Patent: Dec. 12, 1995

[54] PROCESS FOR THE SYNTHESIS OF ALKYLATED AROMATIC HYDROCARBONS

[75] Inventor: Jean-Pierre Ganhy, Brussels, Belgium

[73] Assignee: Solvay Interox (Société Anonyme), Brussels, Belgium

[21] Appl. No.: 204,305

[22] PCT Filed: Sep. 2, 1992

[86] PCT No.: PCT/EP92/02026

§ 371 Date: May 19, 1994

§ 102(e) Date: May 19, 1994

[87] PCT Pub. No.: WO93/05001

PCT Pub. Date: Mar. 18, 1993

Related U.S. Application Data

[63] Continuation-in-part of Ser. No. 768,988, Jan. 24, 1992, Pat. No. 5,288,936.

[30] Foreign Application Priority Data

Sep. 12, 1991 [BE] Belgium ............................ 09100850

[51] Int. Cl.[6] ............................................ C07C 2/66
[52] U.S. Cl. ............................ 585/452; 585/446; 585/467
[58] Field of Search ............................ 585/446, 452, 585/453, 455, 467

[56] References Cited

U.S. PATENT DOCUMENTS

| | | | |
|---|---|---|---|
| 2,758,140 | 8/1956 | Ipatieff et al. | 585/435 |
| 4,962,254 | 9/1990 | Fukao et al. | 585/452 |
| 5,288,936 | 2/1994 | Ganhy et al. | 585/452 |

FOREIGN PATENT DOCUMENTS

| | | |
|---|---|---|
| 2647438 | 11/1990 | France. |
| 1259535 | 1/1972 | United Kingdom. |
| 90/14323 | 11/1990 | WIPO. |

*Primary Examiner*—P. Achutamurthy
*Attorney, Agent, or Firm*—Spencer, Frank & Schneider

[57] ABSTRACT

Process for the synthesis of alkylated aromatic hydrocarbons containing a saturated alkyl chain comprising at least four carbon atoms, according to which an aromatic hydrocarbon substituted by a saturated short-chain alkyl group comprising one to three carbon atoms is reacted with an olefin in the presence of a catalyst which comprises at least one alkali metal or one alkali metal hydride impregnated on an alumina support and the catalyst is prepared in the reaction medium in the presence of the aromatic hydrocarbon containing a short alkyl chain by mixing anhydrous alumina with the alkali metal hydride or with the alkali metal, the ratio by weight of the alkali metal or of the alkali metal hydride to the alumina support being between 0.6 and 1.8. Use of the process for the synthesis of tert-amylbenzene by alkylation of cumene with ethylene.

14 Claims, No Drawings

PROCESS FOR THE SYNTHESIS OF ALKYLATED AROMATIC HYDROCARBONS

CROSS-REFERENCE TO RELATED APPLICATION

The present application is a continuation-in-part of application No. 07/768,988 filed Jan. 24, 1992, now U.S. Pat. No. 5,288,936.

FIELD OF THE INVENTION

The present invention relates to a process for the manufacture of alkylated aromatic hydrocarbons. More particularly, it relates to The manufacture of alkylated aromatic hydrocarbons containing an alkyl chain comprising at least four carbon atoms by condensation of an aromatic hydrocarbon, substituted by a short-chain alkyl group containing 1 to 3 carbon atoms, with an olefin in the presence of a catalyst.

TECHNOLOGY REVIEW

Application FR-A-2,647,438 (INTEROX) discloses a process for the synthesis of alkylated aromatic hydrocarbons which consists in reacting an aromatic hydrocarbon, substituted by a short-chain alkyl group, with an olefin in the presence of a catalyst prepared in the reaction medium by mixing anhydrous alumina with an alkali metal or an alkali metal hydride. The alkali metal/alumina or alkali metal hydride/alumina ratio by weight is preferably between 0.02 and 0.5.

It has been surprisingly found that it was possible to greatly increase the productivity of the reaction if the alkali metal/alumina or alkali metal hydride/alumina ratio by weight was adjusted so that it lies in a range of higher values.

SUMMARY OF THE INVENTION

To this end, the invention relates to a process for the synthesis of alkylated aromatic hydrocarbons containing a saturated alkyl chain comprising at least four carbon atoms, according to which an aromatic hydrocarbon substituted by a saturated short-chain alkyl group containing one to three carbon atoms is reacted with an olefin in the presence of a catalyst which comprises at least one alkali metal or one alkali metal hydride impregnated on an alumina support, the catalyst being prepared in the reaction medium in the presence of the aromatic hydrocarbon containing a short alkyl chain by mixing anhydrous alumina with the alkali metal or with the alkali metal hydride; according to the invention, the ratio by weight of the alkali metal or of the alkali metal hydride to the alumina support is between 0.6 and 1.8.

DETAILED DESCRIPTION OF THE INVENTION

The invention is targeted at preparing aromatic hydrocarbons alkylated by a saturated, linear or branched alkyl chain comprising more than four and, preferably, not more than eight carbon atoms. It applies in particular to the preparation of benzene hydrocarbons alkylated by a saturated and branched alkyl chain comprising five carbon atoms. It is very particularly suited to the preparation of amylbenzenes such as, for example, tert-amylbenzene.

Alkylated aromatic hydrocarbon containing a short chain used as starting material according to the invention is understood to denote any aromatic hydrocarbon containing one or a number of aromatic rings containing five or six carbon atoms and at least one saturated alkyl side chain comprising one to three carbon atoms. Benzene hydrocarbons containing a single aromatic ring are preferred and very particularly toluene, dimethyl and trimethylbenzenes, ethylbenzene, ethyltoluenes, n-propylbenzene and cumene.

The olefin used as alkylating agent must contain a linear carbon chain comprising at least two and not more than five carbon atoms, at least two of them being bonded by an unsaturated olefin-type bond. Monoolefins which only have a single unsaturation are preferred. By way of examples, the following olefins can be used in the process according to the invention: ethylene, propylene, n-butenes, isobutene, butadiene, n-pentenes and methylbutenes.

The catalyst used in the process according to the invention must contain at least one alkali metal or one alkali metal hydride in addition to the alumina support. Any alkali metal may be suitable. Sodium or sodium hydride are, however, generally preferred due to their good activity and their ready availability. Sodium can be the only alkali metal present with the alumina support; such a catalyst has given excellent results.

A variant of the catalyst in accordance with the process according to the invention consists in using an alumina support and a mixture of alkali metals or of alkali metal hydrides in substantially equal proportions or, in another variant, such that a single one of the alkali metals or of the alkali metal hydrides does not exceed double the proportion of all the other combined alkali metals or alkali metal hydrides.

Another particularly advantageous variant of the catalyst in accordance with the process according to the invention consists in mixing, with a main alkali metal or with an alkali metal hydride, small amounts, not exceeding a few percent, of one or of two other alkali metals or alkali metal hydrides as promoters and of adding them to the alumina support. The mixture of sodium or of sodium hydride with more than 0.1% of rubidium and/or of caesium or of rubidium and/or caesium hydride is very particularly worthy of interest. Likewise, it is advantageous that the mixture of sodium or of sodium hydride with rubidium and/or caesium or rubidium hydride and/or caesium hydride contains less than 5% of rubidium and/or of caesium or less than 5% of rubidium hydride and/or of caesium hydride.

It is also possible to combine, in the same catalyst, a mixture of alkali metal with an alkali metal hydride.

The amounts of alkali metal or alkali metal hydride used are preferably such that the catalyst has an alkali metal/alumina or alkali metal hydride/alumina ratio by weight greater than 0.7. It is also advantageous that this ratio by weight is less than 1.5.

According to the invention, the alumina support can consist of alumina of different, pure or mixed, crystalline varieties. The $\alpha$-, $\beta$- and $\gamma$-alumina varieties are well suited. Good results were obtained with a support consisting solely of $\gamma$-alumina.

The aluminas used as catalyst support in the process according to the invention are porous substances. They generally have a mean pore diameter greater than 0.1 nm. Likewise, this mean pore diameter is often less than 500 nm. Advantageous results were obtained with aluminas in which the mean pore diameter was greater than 2 nm. Good results were also obtained with aluminas in which the mean pore diameter was less than 100 nm. The best results were obtained by using aluminas with a mean pore diameter of 20 and 30 nm.

In order for the catalyst obtained by mixing an alkali metal or an alkali metal hydride with these aluminas to be efficient, the specific surface of these aluminas must generally be greater than 10 m$^2$/g. It is also advisable that the specific surface of these aluminas is less than 360 m$^2$/g. In practice, aluminas are preferred in which the specific surface is greater than 50 m$^2$/g. Likewise, aluminas in which the specific surface is less than 200 m$^2$/g are preferred.

The aluminas which are suitable for accompanying the alkali metals in the catalysts in accordance with the process according to the invention generally have a pore volume greater than 25 ml/100 g and preferably greater than 45 ml/100 g. The pore volume of these aluminas is most often less than 75 ml/100 g and preferably less than 65 ml/100 g.

The aluminas used must be free of traces of free water. If necessary, it can be useful, prior to their use as alkali metal support, to calcine them at a temperature greater than 200° C. with the aim of removing any trace of residual moisture. The calcination temperature of these aluminas most often does not exceed 600° C.

The optimum amounts of catalyst are not critical. However, it is advisable, to ensure that the catalyst has a good efficiency, that the ratio by weight of the alkali metal to the short-chain aromatic hydrocarbon is greater than 0.0015. Likewise, it is advantageous that this ratio by weight remains below 0.03.

An advantageous variant of the process according to the invention consists in adding a promoter such as potassium hydroxide during the preparation of the catalyst in the reaction medium. Potassium hydroxide is generally used in an amount such that the K hydroxide/alkali metal or alkali metal hydride ratio by weight is equal to or greater than 0.3 and preferably equal to or greater than 0.5. This ratio by weight is also often less than 2 and preferably than 1.5.

The temperature and the pressure at which the alkylation reaction in accordance with the process according to the invention is carried out must be suited to the nature of the starting aromatic hydrocarbon and olefin. However, it was observed that pressures greater than 0.5 MPa and temperatures greater than 110° C. are well suited. Likewise, it was observed that appropriate pressures are generally less than 10 MPa and that the temperatures are often below 250° C. Pressures greater than 1 MPa and temperatures greater than 170° C. have given the best results. The latter are also obtained with pressures below 5 MPa and temperatures lower than 200 C. and preferably lower than or equal to 198° C. When the reaction is carried out in the vapour phase, it is advantageous to set the respective pressures of the olefin and starting aromatic hydrocarbon so that the olefin/aromatic hydrocarbon molar ratio is greater than 0.7. Likewise, in this case, it is also advantageous that this molar ratio is less than 1.3. An olefin/aromatic hydrocarbon molar ratio in the region of 1 will preferably be chosen.

In order to ensure good contact between the reactants, it is generally necessary to carry out the reaction with vigorous stirring, in particular when the starting hydrocarbon is liquid and the olefin is gaseous under the reaction conditions. All known types of stirrers are generally well suited. The choice of a specific stirrer is made according to the type of equipment used for the reactor.

The reaction in accordance with the process according to the invention can be carried out without distinction in a continuous or non-continuous reactor. When the reaction uses a system containing two different phases, the continuous reactors can be chosen from conventional reactors such as stationary-bed reactors, fluidized beds or mobile-bed reactors which make it possible for the catalyst to move and optionally to be regenerated. If three phases are simultaneously present in the reaction system, it is possible to use conventional continuous stationary-bed (trickle bed) or slurry reactors. In the case of a non-continuous reactor, an autoclave equipped with a paddle stirrer is generally used.

The process according to the invention is particularly well suited to the synthesis of tert-amylbenzene by alkylation of cumene with ethylene.

The examples which follow have the aim of illustrating the invention without limiting the scope thereof.

EXAMPLES 1R and 2R (not in accordance with the invention)

200 ml of cumene, 1 g of sodium hydride, 0.5 g of KOH and a certain amount of alumina were introduced into an autoclave with a capacity of 400 ml equipped with a paddle stirrer.

The autoclave was then closed and heated at 170° C. for 15 minutes with stirring and under a nitrogen purge. The reaction was then initiated by injecting ethylene at a pressure of 1 MPa into the reactor.

The reaction was left to continue for one hour, after which the tert-amylbenzene formed and the residual cumene were quantitatively determined. The results were recorded in the following table.

| No. of the example | NaH/Al$_2$O$_3$ ratio by weight | Degree of conversion of the cumene, % | Productivity g TAB/h · g cat. |
|---|---|---|---|
| 1R | 0.5 | 99.0 | 58.2 |
| 2R | 2.0 | 0.0 | 0.0 |

In this table, the degree of conversion of the cumene is equal to 100 times the molar ratio of the cumene consumed to the cumene used and the productivity is equal to the weight in g of tert-amylbenzene (TAB) formed per hour and per g of catalyst.

EXAMPLES 3 to 5 (according to the invention)

Example 1 was reproduced while varying the weight of alumina.

The results obtained are given in the following table:

| No. of the example | NaH/Al$_2$O$_3$ ratio by weight | Degree of conversion of the cumene, % | Productivity g TAB/h · g cat. |
|---|---|---|---|
| 3 | 0.6 | 99.5 | 64.5 |
| 4 | 0.8 | 98.7 | 74.5 |
| 5 | 1.0 | 98.7 | 81.5 |

What is claimed is:

1. A process for the synthesis of an alkylated aromatic hydrocarbon containing a saturated alkyl chain comprising at least four carbon atoms, comprising:

reacting an aromatic hydrocarbon substituted by a saturated short-chain alkyl group containing one to three carbon atoms with an olefin in the presence of a catalyst of at least one alkali metal or one alkali metal hydride impregnated on an alumina support, said alkali metal or alkali metal hydride having a weight ratio to said alumina support between 0.6 an 1.8, said catalyst being prepared in the reaction medium in the presence of the aromatic hydrocarbon containing a short alkyl chain by mixing anhydrous alumina with the alkali metal or with the alkali metal hydride, and, recovering an alkylated aromatic hydrocarbon containing a saturated alkyl chain comprising at least four carbon atoms.

2. The process according to claim 1, wherein the alumina support has a mean pore diameter of between 2 and 100 nm.

3. The process according to claim 1, wherein the alumina support consists of γ-alumina.

4. The process according to claim 1, wherein the alumina support has a pore volume of between 25 and 75 ml/100 g of alumina and a specific surface area of between 10 and 360 m$^2$/g of alumina.

5. The process according to claim 1, wherein the ratio by weight of the alkali metal or of the alkali metal hydride to the short-chain aromatic hydrocarbon lies in the range of from 0.0015 to 0.03.

6. The process according to claim 1, wherein the alkali metal is sodium and the alkali metal hydride is sodium hydride.

7. The process according to claim 1, wherein the reaction is carried out at a temperature between 170° and 200° C.

8. A process according to claim 1 wherein said aromatic hydrocarbon is cumene and said olefin is ethylene.

9. A process according to claim 2 wherein said aromatic hydrocarbon is cumene and said olefin is ethylene.

10. A process according to claim 3 wherein said aromatic hydrocarbon is cumene and said olefin is ethylene.

11. A process according to claim 4 wherein said aromatic hydrocarbon is cumene and said olefin is ethylene.

12. A process according to claim 5 wherein said aromatic hydrocarbon is cumene and said olefin is ethylene.

13. A process according to claim 6 wherein said aromatic hydrocarbon is cumene and said olefin is ethylene.

14. A process according to claim 7 wherein said aromatic hydrocarbon is cumene and said olefin is ethylene.

* * * * *